US011426463B2

(12) United States Patent
Loupis et al.

(10) Patent No.: US 11,426,463 B2
(45) Date of Patent: Aug. 30, 2022

(54) COMPOSITIONS AND METHODS FOR BIOPHOTONIC BONE RECONSTRUCTION

(71) Applicant: KLOX Technologies Inc., Laval (CA)

(72) Inventors: Nikolaos Loupis, Athens (GR); Remigio Piergallini, Grottammare Ascoli Piceno (IT)

(73) Assignee: KLOX TECHNOLOGIES INC., Laval (CA)

( * ) Notice: Subject to any disclaimer, the term of this patent is extended or adjusted under 35 U.S.C. 154(b) by 138 days.

(21) Appl. No.: 14/403,549

(22) PCT Filed: May 30, 2013

(86) PCT No.: PCT/CA2013/000532
§ 371 (c)(1),
(2) Date: Nov. 24, 2014

(87) PCT Pub. No.: WO2013/177686
PCT Pub. Date: Dec. 5, 2013

(65) Prior Publication Data
US 2015/0119789 A1    Apr. 30, 2015

Related U.S. Application Data

(60) Provisional application No. 61/777,894, filed on Mar. 12, 2013, provisional application No. 61/653,101, filed on May 30, 2012.

(51) Int. Cl.
| | |
|---|---|
| *A61K 41/00* | (2020.01) |
| *C08K 3/32* | (2006.01) |
| *C08K 5/1545* | (2006.01) |
| *C08K 5/00* | (2006.01) |
| *A61L 24/00* | (2006.01) |
| *A61L 27/54* | (2006.01) |
| *A61L 27/46* | (2006.01) |
| *A61N 5/06* | (2006.01) |
| *A61K 6/838* | (2020.01) |

(52) U.S. Cl.
CPC .......... *A61K 41/0057* (2013.01); *A61K 41/00* (2013.01); *A61L 24/0015* (2013.01); *A61L 24/0084* (2013.01); *A61L 27/46* (2013.01); *A61L 27/54* (2013.01); *A61N 5/062* (2013.01); *C08K 3/32* (2013.01); *C08K 5/0041* (2013.01); *C08K 5/1545* (2013.01); *A61K 6/838* (2020.01); *A61L 2300/442* (2013.01); *A61N 2005/0663* (2013.01); *C08K 2003/325* (2013.01)

(58) Field of Classification Search
None
See application file for complete search history.

(56) References Cited

U.S. PATENT DOCUMENTS

| | | | | |
|---|---|---|---|---|
| 7,172,629 | B2 * | 2/2007 | McKay | A61K 38/1875 623/23.61 |
| 2007/0166368 | A1 | 7/2007 | Singh | |
| 2007/0166369 | A1 | 7/2007 | Neuberger et al. | |
| 2010/0036503 | A1 | 2/2010 | Chen et al. | |
| 2011/0033540 | A1 * | 2/2011 | Daniloff | A61K 9/19 424/484 |
| 2011/0224675 | A1 * | 9/2011 | Tofighi | A61B 17/8811 606/94 |
| 2012/0101535 | A1 | 4/2012 | Atkinson et al. | |

FOREIGN PATENT DOCUMENTS

| | | | |
|---|---|---|---|
| CA | 2118218 A1 | 10/1993 | |
| CA | 2496449 A1 | 2/2004 | |
| CA | 2547461 A1 | 6/2005 | |
| CA | 2634245 A1 | 7/2007 | |
| CA | 2767889 A1 | 1/2011 | |
| CN | 1285193 A | 2/2001 | |
| GR | WO 2011006263 A1 * | 1/2011 | ......... A61K 31/4166 |
| JP | 2005538757 A | 12/2005 | |
| JP | 2007515196 A | 6/2007 | |
| JP | 2007197371 A | 8/2007 | |
| JP | 2009511425 A | 3/2009 | |
| JP | 2010511474 A | 4/2010 | |
| JP | 2010535071 A | 11/2010 | |
| RU | 2000109319 A | 2/2003 | |
| RU | 2217171 C2 | 11/2003 | |
| WO | 2004011053 A1 | 2/2004 | |
| WO | 2005034726 A2 | 4/2005 | |
| WO | 2007027092 A2 | 3/2007 | |
| WO | 2008069686 A1 | 6/2008 | |
| WO | 2009018555 A1 | 2/2009 | |

OTHER PUBLICATIONS

Chemical Book, available at <http://www.chemicalbook.com/productchemicalpropertiescb2131094_en.htm>, as accessed Dec. 27, 2016.*
Waveguide, retrieved from the Internet at https://en.wikipedia.org/wiki/Waveguide on Jul. 11, 2019 (Year: 2019).*
Schuckert et al., "De novo grown bone on exposed implant surfaces using photodynamic therapy and recombinant human bone morphogenetic protein-2: Case report," Implant Dentistry, 15(4): 361-365 (2006).
Shibli et al., "Lethal photosensitization and guided bone regeneration in treatment of peri-implantitis: An experimental study in dogs," Clinical Oral Implants Research, 17, pp. 273-281 (2006).

(Continued)

*Primary Examiner* — David J Blanchard
*Assistant Examiner* — Daniel F Coughlin
(74) *Attorney, Agent, or Firm* — BCF LLP

(57) ABSTRACT

This disclosure provides biophotonic compositions comprising a photoactivator, a calcium phosphate mineral, hyaluronic acid and optionally glucosamine. The compositions of this disclosure have utility in the augmentation, repair and/or regeneration of bone when used in conjunction with actinic light of a wavelength absorbed by the photoactivator.

27 Claims, 6 Drawing Sheets

(56) References Cited

OTHER PUBLICATIONS

International Search for PCT/CA2013/000532 dated Sep. 17, 2013.
English Abstract of JP2009511425A retrieved from https://worldwide.espacenet.com/ on Jun. 27, 2018.
English Machine Translation of JP2007197371A retrieved from http://translationportal.epo.org/ on Jun. 27, 2018.
English Abstract of JP2005538757A retrieved from https://worldwide.espacenet.com/ on Jun. 27, 2018.
English Abstract of JP2007515196A retrieved from https://worldwide.espacenet.com/ on Jun. 27, 2018.
English Abstract of JP2010511474A retrieved from https://worldwide.espacenet.com/ on Jun. 27, 2018.
English Abstract of JP2010535071A retrieved from https://worldwide.espacenet.com/ on Jun. 27, 2018.
English Machine Translation of RU2217171C2 retrieved from http://translationportal.epo.org/ on Jun. 27, 2018.
Notification of Reasons for Refusal issued by the Japanese Patent Office dated Nov. 4, 2017 in connection with the Japanese corresponding Application No. 2015-514302 and retrieved from https://register.epo.org/ on Jun. 27, 2018.
Search Report issued by the Russian Patent Office dated May 18, 2017 in connection with the Russian corresponding Application No. 2014147975.
Abstract of the Scientific Publication of Pilloni A. et al., The Effect of Hyaluronan on Mouse Intramembranous Osteogenesis in vitro, Cell. Tissue Res., Nov. 1998, 294(2), pp. 323-333.
Ballini A. et al., Esterified Hyaluronic Acid and Autologous Bone in the Surgical Correction of the Infra-Bone Defects, Int. J. Med. Sci., 2009, 6(2), pp. 65-71.
Fouassier et al., "Dyes as photoinitiators or photosensitizers of polymerization reactions", Materials 2010, 3, 5130-5142.

* cited by examiner

COMPOSITIONS AND METHODS FOR BIOPHOTONIC BONE RECONSTRUCTION

RELATED APPLICATIONS

This application is a national stage filing under 35 U.S.C. § 371 of International Application No. PCT/CA2013/000532, filed on May 30, 2013, which claims the benefit of the filing date under 35 U.S.C. § 119(e) to U.S. Provisional Application 61/653,101, filed on May 30, 2012, U.S. Provisional Application 61/777,894, filed Mar. 12, 2013, the entire contents of which are hereby incorporated by reference. International Application No. PCT/CA2013/000532 was published under PCT Article 21(2) in English.

FIELD OF THE DISCLOSURE

The present disclosure relates to compositions and methods for the augmentation, repair and/or regeneration of bone.

BACKGROUND OF THE DISCLOSURE

The rapid and effective repair of bone defects caused by injury, disease, wounds, fracture, surgery, etc., has long been a goal of orthopedic medicine. To this end, a number of compositions have been used or proposed for use in bone reconstruction. The biological, physical, and mechanical properties of the compositions are among the major factors influencing their suitability and performance in various orthopedic applications.

SUMMARY OF THE DISCLOSURE

The present disclosure provides compositions useful for bone reconstruction. Without being bound by theory, the compositions may promote bone reconstruction by, for example, promoting one or more of growth, repair and/or maintenance of bone tissue at a particular site. Some embodiments of the present disclosure may be used in clinical applications, such as spinal procedures, orthopedic procedures, maxillofacial and dental procedures. Moreover the present disclosure provides methods for applying such compositions, such as, to a bone cavity or defect, e.g., a site of bone loss. The compositions of the disclosure are biophotonic and facilitate growth, recruitment and/or maintenance of bone tissue at the site of application, such as in oral bone cavities or other types of bone cavities. From a broad aspect, there is provided a composition comprising a photoactivator which can absorb and emit light, a calcium phosphate mineral; and hyaluronic acid. Preferably the photoactivator can absorb and emit visible light in the range of about 400-700 nm.

In a first aspect, the disclosure provides a composition comprising: at least 0.2% eosin by weight of the total weight of the composition; a calcium phosphate mineral; and cross-linked hyaluronic acid.

In a second aspect, the disclosure provides a composition comprising: eosin; a calcium phosphate mineral having an average particle size of less than 500 nanometers; and cross-linked hyaluronic acid.

In a third aspect, the disclosure provides a composition comprising: eosin; a calcium phosphate mineral; and cross-linked hyaluronic acid, wherein the composition promotes detectable bone growth in a bone cavity in less than 3 months, or less than about 3.5 months.

In a fourth aspect, the disclosure provides a composition comprising: at least 0.2% of a photoactivator by weight of the total weight of the composition; a calcium phosphate mineral; and cross-linked hyaluronic acid. In certain embodiments, the photoactivator is a fluorescein derivative or a xanthene dye.

In a fifth aspect, the disclosure provides a composition comprising: a photoactivator; a calcium phosphate mineral having an average particle size of less than 500 nm; and cross-linked hyaluronic acid. In certain embodiments, the photoactivator is a fluorescein derivative or a xanthene dye.

In a sixth aspect, the disclosure provides a composition comprising: at least about 0.2% eosin by weight of the total weight of the composition; a calcium phosphate mineral; hyaluronic acid; and glucosamine.

In a seventh aspect, the disclosure provides a composition comprising: eosin; a calcium phosphate mineral having an average particle size of less than about 500 nm; hyaluronic acid; and glucosamine.

In an eighth aspect, the disclosure provides a composition comprising: eosin; a calcium phosphate mineral; hyaluronic acid and glucosamine, wherein the composition promotes detectable bone growth in a treatment site in less than about 3 months following placement of the composition in the treatment site.

In a ninth aspect, the disclosure provides a composition comprising: at least 0.2% photoactivator by weight of the total weight of the composition; a calcium phosphate mineral; hyaluronic acid; and glucosamine.

In a tenth aspect, the disclosure provides a composition comprising: a photoactivator; a calcium phosphate mineral having an average particle size of less than about 500 nm; hyaluronic acid; and glucosamine.

The disclosure contemplates that any of the embodiments set forth below can be combined with each other or with any of the aspects or embodiments set forth above, or otherwise set forth herein.

In certain embodiments of any of the foregoing or following, the composition does not include an oxidant. In certain embodiments, the composition does not include an oxidant selected from hydrogen peroxide, carbamide peroxide and benzoyl peroxide. In certain embodiments, the composition does not include a peroxide. In certain embodiments, the composition does not include a molecule which can generate free-radicals. In certain embodiments, the composition does not include a photoinitiator, or a monomer, or both.

In certain embodiments of any of the foregoing or following, the composition does not include one or more (e.g., 1, 2 or 3) of triethanolamine (TEA), N-vinyl-2-pyrrolidone (NVP), or N-vinyl caprolactam (NVC). In certain embodiments, the composition does not include any of triethanolamine (TEA), N-vinyl-2-pyrrolidone (NVP), or N-vinyl caprolactam (NVC).

In certain embodiments of any of the foregoing or following, the composition does not include a 15 amino acid residue peptide irreversibly bound to the calcium phosphate mineral. In certain embodiments, the composition does not include PepGen P-15. In certain embodiments, the composition does not include a 15 amino acid residue peptide irreversibly bound to hydroxyapatite.

In certain embodiments of any of the foregoing or following, the calcium phosphate mineral comprises hydroxyapatite. In certain embodiments, the hydroxyapatite is or includes hydroxyapatite calcium phosphatetribasic.

In certain embodiments of any of the foregoing or following, the composition is a sterile composition. In certain embodiments, the composition can be sterilized by heat and/or pressure, such as using an autoclave. In certain embodiments, the composition can be sterilized by gamma irradiation. In certain embodiments, sterilization may cause changes in water content which may affect the consistency of the sterilized composition. In these cases, the water content or other the content of other ingredients in the composition can be adjusted appropriately prior to sterilization to compensate for these changes.

In certain embodiments of any of the foregoing or following, the calcium phosphate mineral has an average particle size of less than 500 nm. In certain embodiments, the calcium phosphate mineral has an average particle size of less than 450, less than 400, less than 350, less than 300, less than 250 nm, or less than 200 nm. In certain embodiments, the calcium phosphate mineral has an average particle size of about 200 nm. In certain embodiments, the calcium phosphate mineral has an average particle size of 150-250 nm, 175-275 nm, 200-250 nm, 200-400 nm, 200-300 nm, 250-500 nm, 250-450 nm, or 300-400 nm. For example, in certain embodiments, the calcium phosphate mineral having any such average particle size comprises hydroxyapatite. In certain embodiments, the hydroxyapatite is or comprises hydroxyapatite calcium phosphatetribasic.

In certain embodiments of any of the foregoing or following, the photoactivator, such as eosin, is unbound.

In certain embodiments of any of the foregoing or following, the eosin is present in an amount of at least 0.2% by weight of the total weight of the composition. In certain embodiments, the eosin is present in an amount of 0.2-1% or 0.2-2% by weight of the total weight of the composition. In some embodiments, eosin is present in an amount of 0.2-0.4%, 0.3-0.5%, 0.4-0.6%, 0.5-0.7%, 0.6-0.8%, 0.7-0.9% or 0.8-1%. In other embodiments, eosin is present in an amount of less than 0.2% (e.g., such as less than 0.2% or less than 0.1%).

In certain embodiments, the calcium phosphate mineral is present in an amount of 10-95% by weight of the total weight of the composition. In certain embodiments, the calcium phosphate mineral is present in an amount of 10-30%, 60-70% or 80-95% by weight of the total weight of the composition. In certain embodiments, the calcium phosphate mineral is 50-70% by weight of the total weight of the composition. In other embodiments, the calcium phosphate mineral is 50-55%, 50-60%, 55-60%, 55-65%, 60-65% or 65-70% by weight of the total weight of the composition. In certain embodiments, the calcium phosphate mineral is 62-65% by weight of the total weight of the composition. In certain embodiments, the calcium phosphate mineral comprises hydroxyapatite. In certain embodiments, the hydroxyapatite is or includes hydroxyapatite calcium phosphatetribasic.

In certain embodiments, hyaluronic acid or the cross-linked hyaluronic acid is present in an amount of 5-90% by weight of the total weight of the composition. In certain embodiments, hyaluronic acid or the cross-linked hyaluronic acid is present in an amount of 70-90%, 30-40% or 5-20% by weight of the total weight of the composition. In certain embodiments, the hyaluronic acid or cross-linked hyaluronic acid is 10-50% by weight of the total weight of the composition. In other embodiments, the hyaluronic acid or cross-linked hyaluronic acid is 10-20%, 15-20%, 20-25%, 20-30%, 25-30%, 30-35%, 30-40%, 40-45%, 45-50%, or 40-50% by weight of the total weight of the composition. In certain embodiments, the composition comprises cross-linked hyaluronic acid at 34-38% by weight of the total weight of the composition. In certain embodiments in which hyaluronic acid is cross-linked, hyaluronic acid is provided in association with poly(dimethyldiallylammonium chloride) (PDDA) or 1,4-butanediol diglycidyl ether (BDDE).

In certain embodiments, the hyaluronic acid is not cross-linked and has a molecular weight of between about 1 million Dalton and 2 million Dalton, about 1.2 million to about 1.8 million Dalton, or about 1.7 million Dalton.

The consistency of the composition may vary. In certain embodiments of any of the foregoing or following, the composition is formulated as a flexible paste or putty. In other words, rather than take the form of a liquid or rigid solid, the composition is a flexible paste or putty. In certain embodiments, the flexible paste or putty has a consistency of soft-dried modeling clay.

The consistency of the composition may be controlled by the relative proportions of the components of the composition. For example, decreasing the amount of hyaluronic acid relative to hydroxyapatite will cause the composition to be more viscous, i.e. less flowable. As the composition becomes more viscous, it may be more putty-like, or even block-like. Similarly, as the composition becomes less viscous, it may be described as a flowable material. However, as a person of ordinary skill in the art would be aware, the states of being "flowable" or "putty-like" or "block-like" may exist along a continuum.

In some embodiments, the consistency of the composition is controlled by modifying the ratio of hydroxyapatite to hyaluronic acid. For example, a ratio of hydroxyapatite to hyaluronic acid of about 1:9, 1.5:8.5, 2:8, 2.5:7.5, 3:7, 3.5:6.5, 4:6 or 4.5:5 will result in a composition that is more flowable. A ratio of hydroxyapatite to hyaluronic acid of about 5.5:4.5, 6:4, 6.5:3.5 or 7:3 will result in a composition that is more putty-like. A ratio of hydroxyapatite to hyaluronic acid of 7.5:2.5, 8:2, 8.5:1.5, 9:1 or 9.5:0.5 will result in a composition that is more block-like. In certain embodiments of any of the foregoing or following aspects or embodiments, the disclosure provides compositions in which the ratio of hydroxyapatite to hyaluronic acid is about (i) 1:9, 1.5:8.5, 2:8, 2.5:7.5, 3:7, 3.5:6.5, 4:6 or 4.5:5 or (ii) 5.5:4.5, 6:4, 6.5:3.5 or 7:3 or (iii) 7.5:2.5, 8:2, 8.5:1.5, 9:1 or 9.5:0.5.

In certain embodiments, the consistency of the composition is controlled by modifying the relative amounts or ratios of calcium phosphate mineral (a solid component) to hyaluronic acid and glucosamine (a liquid component). For example, the hyaluronic acid and glucosamine together can be about 10-90% by weight of the total weight of the composition, or about 10-70%, about 30-40%, or about 70-90% by weight of the total weight of the composition. The ratio of the solid component to the liquid component can be about 1:9, 1.5:8.5, 2:8, 2.5:7.5, 3:7, 6:4, 6.5:3.5, 7:3, 8:2, 8.5:1.5, 9:1 or 9.5:0.5.

The consistency of the composition can also be controlled by modifying the relative amounts or ratios of the hyaluronic acid and glucosamine. For example, the ratio of hyaluronic acid to glucosamine can be about 1:1, 3:2, 7:3, 4:1; or 9:1.

In an eleventh aspect, the disclosure provides a pharmaceutical package comprising a container comprising a composition of the disclosure; and instructions for using the composition.

In a twelfth aspect, the disclosure provides a pharmaceutical package or a kit comprising one or more containers comprising the following ingredients: a photoactivator such as eosin; a calcium phosphate mineral having an average particle size of less than 500 nm; and either cross-linked hyaluronic acid or glucosamine and non-crosslinked hyaluronic acid. The package/kit may further comprise instructions for formulating a composition comprising the ingredients; and instructions for using the formulated composition. The package/kit may further comprise a device for mixing and/or applying the composition, such as a mixing tool, or a spatula. The package/kit may further comprise a syringe for injecting the composition and/or a light source.

In a thirteenth aspect, the disclosure provides a method of bone augmentation, repair or regeneration. The method comprises: providing a composition of the disclosure and applying a layer of the composition to a bone cavity. The composition that has been applied is then irradiated with actinic light. The step of applying a layer of composition and then irradiating with actinic light is repeated at least once to fill the bone cavity (or some other region in which additional bone is needed or desired) with the composition. In certain embodiments, the steps of applying a layer of composition and then irradiating with actinic light is repeated at least 2, 3, 4 or at least 5 times. The composition can be applied using an appropriate instrument such as a cement packer, or it can be injected. Following application of the composition into the bone cavity and irradiation of light, the method may further comprise placing a suture over the filled cavity. Alternatively, the composition may be applied in a single layer.

In a fourteenth aspect, the method comprises a method of preparing a bone site for a dental implant. This may include disinfecting the bone site. The method can further comprise application of one or more layers of the composition and subsequent irradiation. The method may further comprise placing an implant into the bone site after a period of time sufficient for adequate replacement bone to form in the bone site, such as after about 1, 2, 3, 4, 5 or 6 months. In certain embodiments of any of the foregoing or following, each layer of composition is applied at a thickness of 0.5-4 millimeters. In certain embodiments, each layer of composition is applied at a thickness of 0.5, 1, 1.5, 2, 2.5, 3, 3.5, or 4 millimeters. When multiple layers of composition are applied, each layer may be the same or a differing thickness. In other words, in certain embodiments, the thickness of each layer is independently selected.

In certain embodiments of any of the foregoing or following, when a layer is irradiated, it is irradiated for a period of 1 second to 5 minutes. In certain embodiments, the composition is irradiated for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes or 4-5 minutes. In certain embodiments, the composition is irradiated for a period of 15 seconds to five minutes. In certain embodiments, the composition is irradiated until substantial photobleaching of the composition occurs. In certain embodiments, photobleaching of the composition is not observed during irradiation. When multiple layers of composition are applied, each layer may be irradiated for the same period of time or for differing periods of time. In other words, in certain embodiments, the time of irradiation is independently selected for each layer.

In certain embodiments of any of the foregoing or following, the composition (each layer of the composition applied) is irradiated with actinic light having a wavelength in the range of 400-800 nm. In other embodiments, the composition is irradiated with actinic light having a wavelength of 400-700, 400-600, 400-500, 450-550, 425-525, 500-600, or 450-550 nm. When multiple layers of composition are applied and irradiated, each layer may be irradiated with light having the same or differing wavelength. In other words, in certain embodiments, the wavelength of the light is independently selected for each layer that is irradiated.

In certain embodiments of any of the foregoing, following application and irradiation of the composition, the composition promotes detectable bone growth in the bone cavity in less than about 3 months. In certain embodiments, the composition promotes detectable bone growth in the bone cavity without promoting detecting growth of soft tissues.

In certain embodiments, the composition can be pre-made and stored.

The disclosure contemplates all combinations of any of the foregoing aspects and embodiments, as well as combinations with any of the embodiments set forth in the detailed description and examples. Moreover, when reference is made to "any of the foregoing aspects or embodiments", it should also be understood to include "any of the foregoing or following aspects or embodiments." As used herein, the term "compositions of the disclosure" should be understood to refer and apply to any of the biophotonic compositions and pharmaceutical compositions described herein. Exemplary compositions of the disclosure comprise a fluorescent dye such as eosin, a calcium phosphate mineral, hyaluronic acid and optionally glucosamine.

DETAILED DESCRIPTION

(i) Overview

Figure 1:
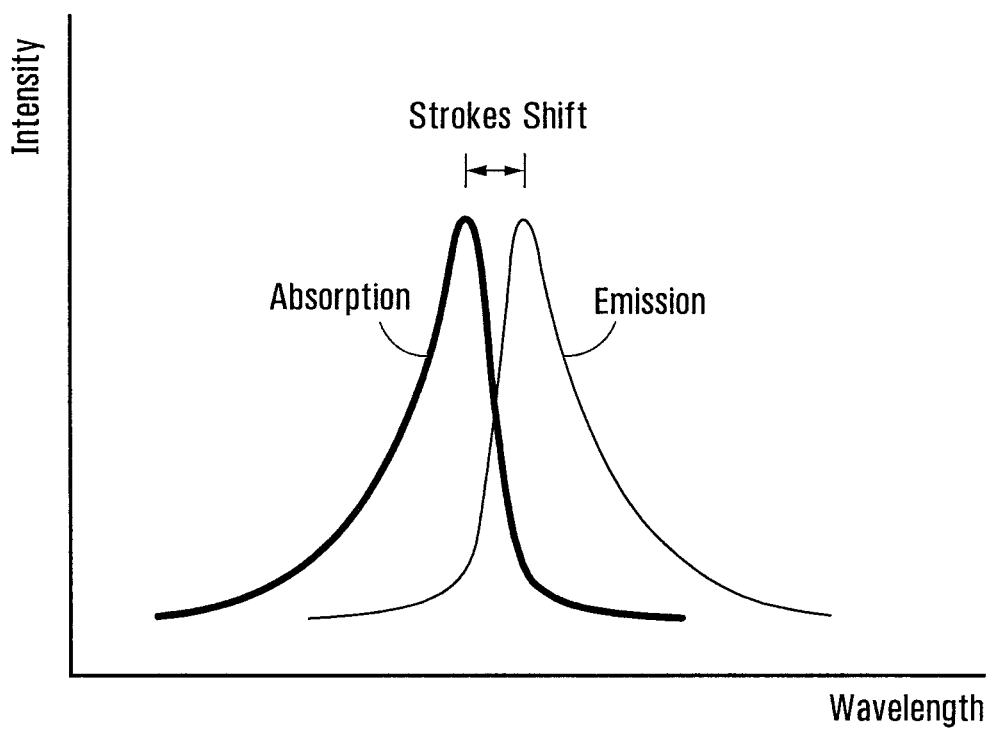
FIG. 1 illustrates the Stokes' shift.

Bone is in a constant state of remodeling. This makes bone a particularly suitable target for developing approaches where the remodeling potential of bone is harnessed to promote bone reconstruction in a patient in need thereof, such as in a patient with an injury, disease, fracture, trauma, or other condition in which the amount of bone tissue present at a site is insufficient.

There are numerous examples where augmentation, repair or growth of the bone tissue present at a particular site is useful. Several of these examples are in the dental arena and involve reconstruction of bone tissue in portions of the jaw. One such example, is for the purpose of preparing a site for placement of a dental implant.

The present disclosure provides biophotonic compositions useful for promoting bone reconstruction. Without being bound by theory, such bone reconstruction may be mediated by any one or more of growth, recruitment and maintenance of bone tissue at a particular site. These compositions may be used in clinical applications, such as spinal procedures, orthopedic procedures, maxillofacial and dental procedures. These compositions are also useful, for example, to augment the available bone at a site prior to placement of a dental implant.

(ii) DEFINITIONS

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "actinic light" is intended to mean light energy emitted from a specific light source (lamp, LED, or laser) and capable of being absorbed by matter (e.g. the photoactivator defined below). In a preferred embodiment, the actinic light is visible light having a wavelength of about 400 to about 700 nm.

The term "photoactivator", "chromophore" or "dye" is intended to mean a chemical compound capable of absorbing actinic light. The photoactivator or chromophore readily undergoes photoexcitation and can then transfer its energy to other molecules or emit the absorbed energy as light.

The term "bone defect" or "bone cavity" refers to a bony structural disruption requiring repair. The defect further can define an osteochondral defect, including a structural disruption of both the bone and overlying cartilage. A defect may assume the configuration of a "void", which is understood to mean a three-dimensional defect such as, for example, a gap, cavity, hole or other substantial disruption in the structural integrity of a bone or joint. A defect may be the result of accident, disease, cyst or tumour removal, teeth extraction, surgical manipulation, and/or prosthetic failure. In certain embodiments, it may be required to augment existing bone such as after a sinus-lift. In certain embodiments, the defect is a void having a volume incapable of endogenous or spontaneous repair. In certain embodiments, the defect may be a fracture.

The term "bone reconstruction" refers to any one or more of the renewal, repair, maintenance and/or augmentation of bone tissue at a particular site such as a bone defect. The term "bone reconstruction" can be used interchangeably herein with "bone regeneration".

The term "oxidant" or "oxygen-releasing agent" is intended to refer to an agent that readily transfers oxygen atoms and oxidizes other compounds, or a substance that gains electrons in a redox chemical reaction.

The term "putty" or "putty-like" refers to compositions of the disclosure having a dough-like or clay-like consistency akin to pliable modeling clay. Compositions having such a consistency are moldable and deformable such that they can be molded into a shape approximating that of a bone cavity or implant site during a procedure.

The term "flowable" refers to a composition of the present disclosure having a gel-like or paste-like consistency, for example, a consistency akin to gel toothpaste. In certain embodiments, flowable compositions may be injectable. In certain embodiments, an injectable composition of the present disclosure may, for example, be introduced between elements or into a confined space in vivo (e.g., between pieces of bone or into the interface between a prosthetic device and bone, among others).

The term "block-like" refers to a composition of the present disclosure having a rigid consistency. A block-like composition of the present disclosure may be brittle and easily broken into pieces with pressure. The block-like composition may be in a shaped form. The block-like composition may be useful for application to treatment sites which need physical support, such as connective tissue flaps to prevent them from collapsing in case of large bone cavities.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

(iii) COMPOSITIONS OF THE DISCLOSURE

The disclosure provides compositions comprising certain active ingredients. These compositions of the disclosure may be described based on the components making up the composition. Additionally or alternatively, the compositions of the disclosure have functional and structural properties and these properties may also be used to define and describe the compositions. Individual active components of the compositions of the disclosure are detailed below.

(a) Photoactivators

Compositions of the disclosure comprise a photoactivator. When a photoactivator absorbs a photon of a certain wavelength, it becomes excited. This is an unstable condition and the molecule tries to return to the ground state, giving away the excess energy. For some chromophores, it is favorable to emit the excess energy as light when returning back to the ground state. This process is called fluorescence. The peak wavelength of the emitted fluorescence is shifted towards longer wavelengths compared to the absorption wavelengths due to loss of energy during the process. This is called the Stokes' shift and is illustrated in FIG. 1. In the proper environment (e.g., in a composition of the present disclosure) much of this energy is transferred to the other components of the composition or to the treatment site directly. Suitable photoactivators can be fluorescent dyes (or stains), although other dye groups or dyes (biological and histological dyes, food colorings, carotenoids) can also be used.

Without being bound to theory, it is thought that fluorescent light emitted by photoactivated chromophores may have therapeutic properties due to its femto-, pico-, or nano-second emission properties which may be recognized by biological cells and tissues, leading to favourable biomodulation. Furthermore, the emitted fluorescent light has a longer wavelength and hence a deeper penetration into the tissue than the activating light. Irradiating tissue with such a broad range of wavelength, including in some embodiments the activating light which passes through the composition, may have different and complementary therapeutic effects on the cells and tissues.

The activated chromophore may also transfer at least some of its energy to an oxygen-releasing agent (oxidant), which in turn can produce for example singlet oxygen which may also have a beneficial therapeutic effect. The oxygen-releasing agents may be found intrinsically at the site of application of the compositions, or be added to the site in conjunction with the compositions of the present invention.

Suitable chromophores can be fluorescent dyes (or stains), although other dye groups or dyes (biological and histological dyes, food colorings, naturally occurring dyes, carotenoids) can also be used. Combining chromophores may increase photo-absorption by the combined dye molecules and enhance absorption and photo-biomodulation selectivity. This creates multiple possibilities of generating new photosensitive, and/or selective chromophore mixtures. Thus, in certain embodiments, compositions of the disclosure include more than one photoactivator.

In certain embodiments, the biophotonic topical composition of the present disclosure comprises a first chromophore which can undergo photobleaching upon application of light. In some embodiments, the first chromophore absorbs at a wavelength in the range of the visible spectrum, such as at a wavelength of about 400-700 nm, about 380-800 nm, 380-700, or 380-600 nm. In other embodiments, the first chromophore absorbs at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm, 250-350 nm, 300-400 nm, 350-450 nm, 400-500 nm, 450-650 nm, 600-700 nm, 650-750 nm or 700-800 nm.

Figure 2:
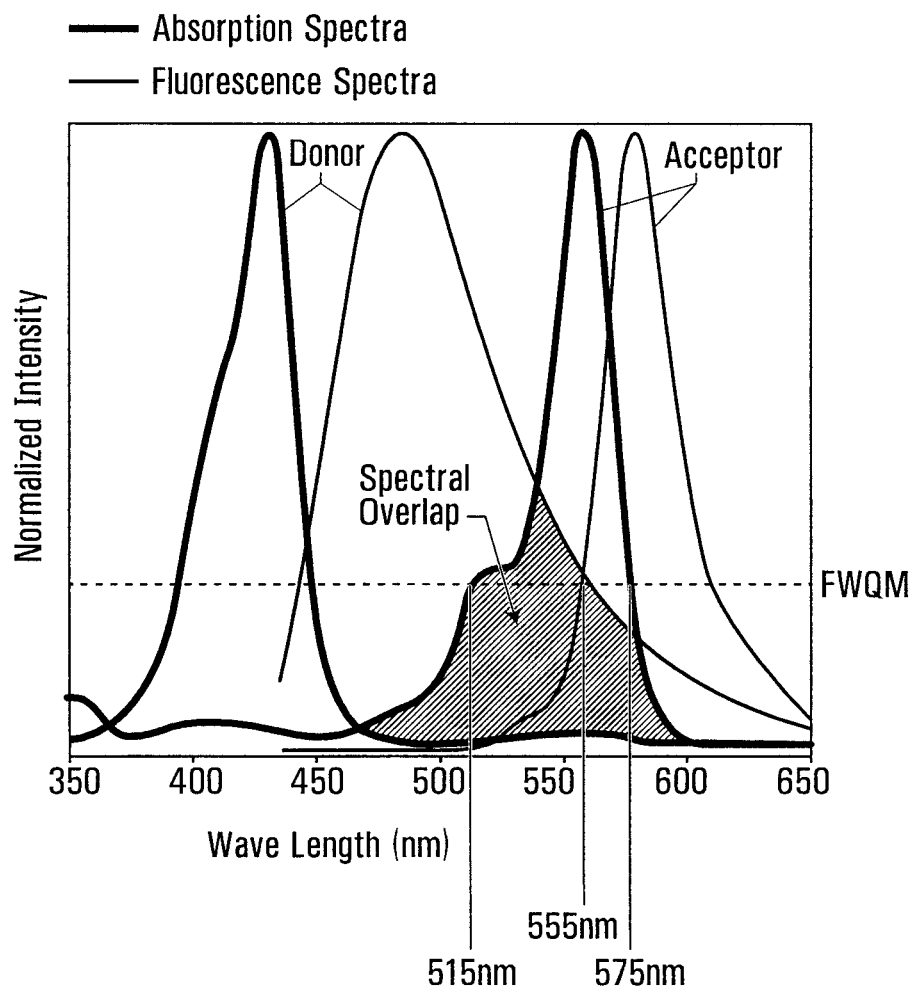
FIG. 2 illustrates the absorption and emission spectra of donor and acceptor chromophores. The spectral overlap between the absorption spectrum of the acceptor chromophore and the emission spectrum of the donor chromophore is also shown.

The biophotonic compositions disclosed herein may include at least one additional chromophore. When such multichromophore compositions are illuminated with light, energy transfer can occur between the chromophores. This process, known as resonance energy transfer, is a widely prevalent photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. More specifically, for energy transfer to occur, the emission spectrum of the donor chromophore must overlap with the absorption spectrum of the acceptor chromophore (FIG. 2).

Figure 3:
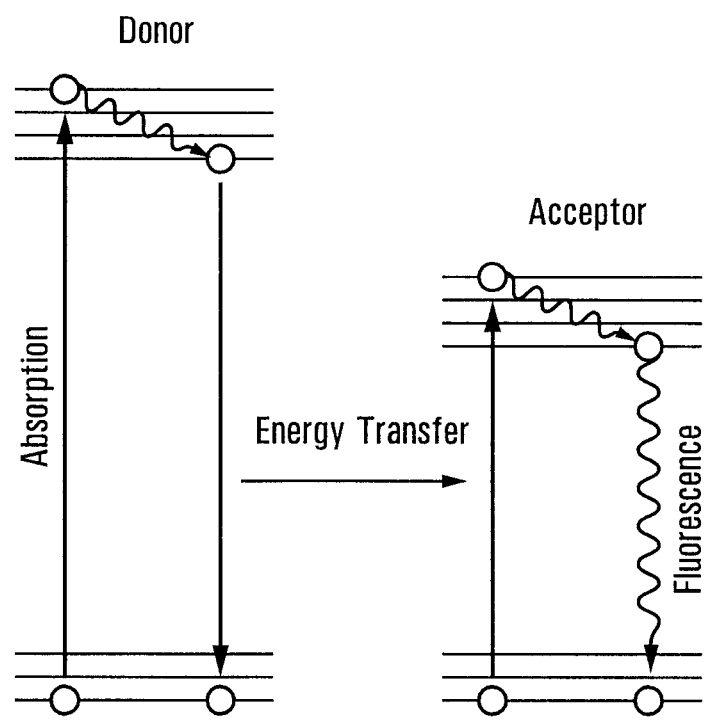
FIG. 3 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, the more overlap there is between the donor chromophores' emission spectra and the acceptor chromophore's absorption spectra, the better a donor chromophore can transfer energy to the acceptor chromophore.

In certain embodiments, the biophotonic topical composition of the present disclosure further comprises a second chromophore. In some embodiments, the first chromophore has an emission spectrum that overlaps at least about 80%, 50%, 40%, 30%, 20%, 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

% spectral overlap, as used herein, means the % overlap of a donor chromophore's emission wavelength range with an acceptor chromophore's absorption wavelength range, measured at spectral full width quarter maximum (FWQM). For example, FIG. 3 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

The first chromophore may be present in an amount more than about 0.2% per weight of the total composition. In certain embodiments, the first chromophore is present in an amount of about 0.2-1%, about 0.2-0.9%, about 0.2-0.8%, about 0.2-0.7%, about 0.2-0.6%, about 0.2-0.5%, about 0.2-0.4%, or about 0.2-0.3%. In certain embodiments, the first chromophore is present in an amount of about 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the first chromophore is present in an amount of at least about 0.2% per weight of the composition.

Optionally, when the biophotonic topical composition comprises a first and a second chromophores, the first chromophore is present in an amount of about 0.05-40% per weight of the composition, and the second chromophore is present in an amount of about 0.05-40% per weight of the composition. In certain embodiments, the total weight per weight of chromophore or combination of chromophores may be in the amount of about 0.05-40.05% per weight of the composition. In certain embodiments, the first chromophore is present in an amount of about 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the first chromophore is present in an amount of at least about 0.2% per weight of the composition. In certain embodiments, the second chromophore is present in an amount of about 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of at least about 0.2% per weight of the composition. In certain embodiments, the total weight per weight of chromophore or combination of chromophores may be in the amount of about 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

Suitable chromophores that may be used in the biophotonic topical compositions of the present disclosure include, but are not limited to the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; amphiphilic chlorophyll derivative 2, and phycobiliproteins.

Xanthene Derivatives

Exemplary xanthene dyes include but are not limited to Eosin B (4',5'-dibromo,2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropyl-benzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Allophycocyanin (APC), Aluminon, Amido black 10B, Amidoschwarz, Aniline blue WS, Anthracene blue SWR, Auramine 0, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red 0, Orange G, Orcein, Pararosanilin, Phloxine B, Picric acid, Ponceau 2R, Ponceau 6R, Ponceau B, Ponceau de Xylidine, Ponceau S, *Primula*, Purpurin, Phycocyanins, Phycoerythrins. Phycoerythrincyanin (PEC), Phthalocyanines, Pyronin B, Pyronin G, Pyronin Y, Rhodamine B, Rosanilin, Rose bengal, Saffron, Safranin 0, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any one or more of the chromophores listed above, or a combination thereof, so as to provide a biophotonic impact at the application site. In other words, chromophores are used in the composition of the present disclosure to promote bone regeneration such as by augmentation of bone, formation of new bone, or repair of bone.

This is a distinct application of these agents and differs from the use of chromophores as simple stains or as photoinitiators in photo-polymerization. Chromophores (dyes) have been used in free-radical photopolymerisation in combination with at least one monomer and at least one entity which can generate free-radicals. In known free-radical systems, chromophores are used in combination with the following: triazine moieties, O-acyloxime, thiols, ketones, amines, onium salts, bromo compounds, triazine derivatives or ferroceniums (see for example, "Dyes as photoinitiators or photosensitizers of polymerization reactions" Fouassier, J P et al, Materials 2010, 3, 5130-5142). The presence of a monomer is also required. In the present compositions, photopolymerisation does not and cannot take place as the present compositions do not include all of the components necessary for photopolymerisation. For example, the present composition does not include at least one or more of a monomer or a free-radical generator. No hardening or stiffening of the present compositions are observed on illumination.

In some embodiments, the combination of chromophores may be synergistic. In some embodiments, the two or more chromophores are both xanthene dyes, for example, Eosin Y as a first chromophore and any one or more of Rose Bengal, Erythrosine, Phloxine B, Fluorescein as a second chromophore. It is believed that these combinations have a synergistic effect as these chromophores can transfer energy to each other when activated. This transferred energy is then emitted as fluorescence or by production of reactive oxygen species. By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

(b) Calcium Phosphate Mineral

Another component of the compositions of the disclosure is a calcium phosphate mineral. In certain embodiments, the calcium phosphate mineral comprises hydroxyapatite. In certain embodiments, the hydroxyapatite is or comprises hydroxyapatite calcium phosphatetribasic (Hap). One source of such calcium phosphate mineral is Sigma Aldrich (e.g., catalog number 677418-10G; Cas 12167-74-7).

Hydroxyapatite is a naturally occurring mineral form of calcium apatite with the formula $Ca_5(PO_4)_3(OH)$ (also written $Ca_{10}(PO_4)_6(OH)_2$ to denote that the crystal unit cell comprises two entities). Hydroxyapatite is the hydroxyl end member of the complex apatite group. The $OH^-$ ion can be replaced by fluoride, chloride or carbonate, producing fluorapatite or chlorapatite. Pure hydroxyapatite powder is white.

Regardless of the particular calcium phosphate mineral used, in certain embodiments, the composition comprises a calcium phosphate mineral having an average particle size of less than 500 nm (e.g., nanoparticles). For example, the calcium phosphate mineral, such as HA, may have an average particle size of less than 500, 450, 400, 350, 300, 250, 200, or even less 150 nanometers. In certain features, the calcium phosphate mineral in the composition has an average particle size of 200 nm or of less than 200 nm.

The use of nanoparticles of calcium phosphate mineral in the composition is somewhat surprising. In numerous other contexts, microparticles are specifically selected to improve the porosity of a material. However, in the context of the disclosure, when nanoparticles are selected, the nanoparticles transmit light and may enhance the desired biophotonic effect of the compositions. In certain embodiments, the particles are observed to form a waveguide network such that light incident on one surface of the composition is observed passing through the composition and being emitted from another surface of the composition. Moreover, the nanoparticles may discourage soft connective tissue growth. This further facilitates bone reconstruction because the infiltration of soft connective tissue can have an inhibitory effect on bone reconstruction. The nanoparticles also confer on the composition a malleable consistency whereby the composition can be formed into any appropriate shape to fill a bone defect, or even can be shaped to replace a partial or complete bone such as a portion of the skull, a radial bone of the wrist etc.

In certain features, the calcium phosphate mineral, such as a calcium phosphate mineral comprising hydroxyapatite, is 10-95% by weight of the total weight of the composition. For example, the calcium phosphate mineral may be 10-30%, 60-70%, or 80-95% by weight of the total weight of the composition.

In certain features, the calcium phosphate mineral, such as hydroxyapatite, is 50-70% by weight of the total weight of the composition. In other embodiments, the calcium phosphate mineral is 50-55%, 50-60%, 55-60%, 55-65%, 60-65% or 65-70% by weight of the total weight of the composition. In certain embodiments, the calcium phosphate mineral is 62-65% by weight of the total weight of the composition.

The calcium phosphate mineral can also be Bioglass® or other glasses containing calcium and phosphate.

(c) Hyaluronic Acid

Hyaluronic acid (Hyaluronan, hyaluronate) is a non-sulfated glycosaminoglycan distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissue hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. Hyaluronic acid is well suited to biological applications and is highly biocompatible.

Compositions of the disclosure comprise hyaluronic acid. The hyaluronic acid in the composition may be cross-linked hyaluronic acid. Exemplary cross-linked hyaluronic acid suitable for use may be obtained in a pre-filled syringe of, for example, 0.6 ml (from Regenyal laboratories, Italy). The syringe may contain 25 mg cross-linked hyaluronic acid in water, such as sterile water. The hyaluronic acid may be a cross-linked biphasic hyaluronan. Optionally, the cross-linked hyaluronic acid may be combined with PDDA, such as 5% PDDA. Other commercially available cross-linked hyaluronic acid derivatives, including Hylaform® (from Biomatrix, USA), Restylane® (from Medicis Aesthetics, USA) or Juvéderm® (from Allergan, USA), are also suitable for use in the composition of the disclosure.

The hyaluronic acid may be a non-cross-linked hyaluronic acid, such as sodium hyaluronate having a molecular weight of at least about 1 million Daltons, between about 1 million and 2 million Da, or about $1.7 \times 10^6$ Da. This hyaluronic acid may be combined with glucosamine.

Without being bound by theory, hyaluronic acid helps confer overall elasticity of the composition and facilitates adherence of the composition when applied. These elasticity and adherence properties of the composition help prevent rejection following application, and also facilitate filling of the defect site with the composition due to malleability of the composition.

Hyaluronic acid also provides a structure or support within the bone defect site during bone remodeling which can prevent collapse of the bone defect site. Hyaluronic acid is a bioresorbable material and will be broken down by the body. Cross-linked hyaluronic acid has a slower rate of degradation than non-cross linked hyaluronic acid. Hyaluronic acids with a higher molecular weight have a slower rate of degradation than hyaluronic acids of lower molecular weight.

In certain features, the cross-linked hyaluronic acid is 5-90% by weight of the total weight of the composition. For example, the cross-linked hyaluronic acid is 70-90%, 30-40%, or 5-20% by weight of the total weight of the composition.

In certain features, the hyaluronic acid or cross-linked hyaluronic acid is 10-50% by weight of the total weight of the composition. In other embodiments, the hyaluronic acid or cross-linked hyaluronic acid is 10-20%, 15-20%, 20-25%, 20-30%, 25-30%, 30-35%, 30-40%, 40-45%, 45-50%, or 40-50% by weight of the total weight of the composition. In certain embodiments, the composition comprises cross-linked hyaluronic acid at 34-38% by weight of the total weight of the composition.

(d) Glucosamine

Glucosamine is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes.

Glucosamine can be combined with hyaluronic acid in embodiments of the present disclosure to provide a naturally-derived biocompatible and bioresorbable filler material for bone defects. The inventors have found that the combination of (1) a non-crosslinked hyaluronic acid with a molecular weight of about 1-2 million Da and (2) glucosamine, can provide comparable bioresorption properties to that of cross-linked hyaluronic acid alone. Furthermore, varying the ratio of glucosamine to the other components of the composition can provide a fine control of the final texture and viscosity of the composition. For example, increasing the content of glucosamine can increase the stickiness of the composition which can improve its adhesion to the walls of the bone defect when placed in a bone defect.

(e) Other Components of the Composition

Certain suitable compositions of the disclosure can also be described based on the absence of certain components from the composition. The examples provided herein may be combined so that a suitable composition may specifically exclude one of these ingredients, two, three, four, five, or any number of the ingredients set forth here. For example, in certain embodiments, the composition does not include an oxidant (oxygen releasing agent) such as hydrogen peroxide, carbamide peroxide and benzoyl peroxide. Certain compositions do not include a peroxide. By way of further example, in certain embodiments, the composition does not include a photoinitiator such as one or more of triethanolamine (TEA), N-vinyl-2-pyrrolidone (NVP), or N-vinyl caprolactam (NVC). Alternatively, the composition, in certain features, does not include any of triethanolamine (TEA), N-vinyl-2-pyrrolidone (NVP), or N-vinyl caprolactam (NVC). In certain embodiments, the composition does not include a monomer. In certain embodiments, the composition does not include all the agents necessary for photopolymerisation to take place.

In certain embodiments, the composition does not include a 15 amino acid residue peptide irreversibly bound to the calcium phosphate mineral. For example, the composition does not include a 15 amino acid residue peptide irreversibly bound to hydroxyapatite, such as observed in a hydroxyapatite product known as Pep Gen P-15. In other words the calcium phosphate material is an unbound hydroxyapatite.

(f) Consistency of the Composition

The consistency of the composition may vary. In certain embodiments, it may be advantageous to adapt the consistency of the composition to the target tissue. In situations in which an open operation allows wide exposure of the target area, a more viscous composition, such as putty, will be useful and can be pressed or molded into the site without difficulty. For example, a bone fracture that is being repaired by open exposure would be ideal for putty consistency. However, if the target is a narrow recess being approached percutaneously with a narrow needle, a less viscous or flowable composition is preferred. For example, when the intended use is to inject the composition into a vertebra, it may be preferred to use a larger gauge needle (e.g. an 8 gauge needle) and therefore the composition can be relatively viscous though much less so than a composition having a putty-like consistency. Alternatively, the intended use may involve injection of the composition into a posterior articulation of the spine, which is a narrow recess that would require a smaller, e.g. 25-gauge needle, to achieve access. For such a procedure a relatively more dilute, less viscous composition is preferred in order to achieve adequate flow. As will be readily understood, adjustments to the overall consistency of the composition will be made according to its intended purpose (e.g. target tissue site).

The consistency of the composition may be controlled by the relative proportions of the components of the composition. For example, decreasing the amount of hyaluronic acid relative to hydroxyapatite will cause the composition to be more viscous, i.e. less flowable.

As the composition becomes more viscous, it may be more putty-like, or even rigid (e.g., block-like). Similarly, as the composition becomes less viscous, it may be described as a flowable material. For example, a flowable composition may have a consistency like gel toothpaste. However, as a person of ordinary skill in the art would be aware, the states of being "flowable" or "putty-like" or "block-like" may exist along a continuum.

In some embodiments, the consistency of the composition is controlled by modifying the ratio of calcium phosphate mineral to hyaluronic acid. For example, in certain embodiments, the consistency of the composition is controlled by modifying the ratio of hydroxyapatite to hyaluronic acid. For example, a ratio of hydroxyapatite to hyaluronic acid of about 1:9, 1.5:8.5, 2:8, 2.5:7.5, 3:7, 3.5:6.5, 4:6 or 4.5:5 will result in a composition that is more flowable. A ratio of hydroxyapatite to hyaluronic acid of about 5.5:4.5, 6:4, 6.5:3.5 or 7:3 will result in a composition that is more putty-like. A ratio of hydroxyapatite to hyaluronic acid of 7.5:2.5, 8:2, 8.5:1.5, 9:1 or 9.5:0.5 will result in a composition that is more rigid (e.g., block-like).

In some embodiments, the consistency of the composition is controlled by modifying the ratio of calcium phosphate mineral, hyaluronic acid and glucosamine. For example, in certain embodiments, the consistency of the composition is controlled by modifying the ratio of a solid component of the composition (calcium phosphate particles) to a liquid component (hyaluronic acid and glucosamine powder dissolved in water). For example, the hyaluronic acid and the glucosamine component are about 10-90%, 10-70%, 70-90%, or 30-40% by weight of the total weight of the composition. The ratio of the solid component to the liquid component can be 1:9, 1.5:8.5, 2:8, 2.5:7.5, 3:7, 6:4, 6.5:3.5, 7:3, 8:2, 8.5:1.5, 9:1 or 9.5:0.5. In certain embodiments, the ratio of the hyaluronic acid to glucosamine can also be varied to control the consistency. For example, the ratio of hyaluronic acid to glucosamine can be about 1:1, 3:2, 7:3, 4:1; or 9:1.

(iv) METHODS OF USE

Compositions of the disclosure, including pharmaceutical compositions and compositions provided as part of a pharmaceutical package, have numerous uses. The compositions of the disclosure are biophotonic and are useful for bone reconstruction. Without being bound by theory, the compositions of the disclosure may help promote the growth, recruitment and survival of bone tissue at a particular site. The compositions are biodegradable. Thus, over a short period of time, bone tissue replaces the composition as that composition degrades. The result is an increase in bone tissue at the site of application of the biophotonic composition of the disclosure.

Given their biocompatibility, biophotonic and bone growth properties, compositions of the disclosure have numerous uses in human and animal patients. For example, compositions of the disclosure may be used to augment, repair or promote growth of bone in a cavity prior to placement of a dental implant. By way of further example, compositions of the disclosure may be used to help promote reconstruction of jaw bone tissue following injury or disease. By way of further example, compositions of the disclosure may be used to help promote reconstruction of complex fractures that have not healed or that have a low likelihood of healing completely. In yet another example, compositions of the disclosure may be used to help promote reconstruction of bone that has been damaged or destroyed by disease, such as cancer, or following excision of bone tissue following a diagnosis of cancer.

In use, the composition is implanted at a site at which bone growth is desired, e.g. to treat a disease, defect or location of trauma, and/or to promote artificial arthrodesis. Bone repair sites that can be treated with the composition of the disclosure include, but are not limited to, those resulting from injury, defects brought about during the course of surgery, infection, malignancy or developmental malformation. The compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc.

For any of these potential applications, compositions of the disclosure may be applied directly to a site where bone reconstruction is needed. Accessing this site may, in some cases, require surgical intervention to expose the site. However, in some cases, the site is already exposed or can be accessed without the need for surgical intervention.

Certain applications of the compositions and methods of the disclosure are in dentistry where they can be used to augment damaged or insufficient jaw bone either alone or in preparation for placement of a dental implant. In either case, the starting point of the method is a patient that has lost (e.g. following extraction) one or more teeth. The tooth loss may be due to any of a variety of circumstances, including decay, disease, or injury. Moreover, a single tooth, several teeth or substantially all of the teeth in one or more quadrants of the mouth may be affected. In this context, the term "dental bone cavity" is used herein to refer to the exposed site in the mouth and jaw left following tooth loss or extraction.

A typical dental implant includes a screw, such as a titanium screw, that resembles a tooth root. In a standard procedure, a dental implant is embedded in the jaw. In its most basic form, the placement of an implant requires a preparation into the bone using either hand osteotomes or precision drills with highly regulated speed to prevent burning or pressure necrosis of the bone. After a variable amount of time to allow the bone to grow on to the surface of the implant, a crown or crowns can be placed on the implant. The amount of time required to place an implant will vary depending on the experience of the practitioner, the quality and quantity of the bone and the difficulty of the individual situation.

To place a dental implant at edentulous (without teeth) jaw sites, a pilot hole is drilled into the recipient bone. This entails some risk, as care must be exercised to avoid damaging vital nerve structures within the jaw. This procedure in particularly risky if the quantity or quality of the bone at the site is sub-optimal. However, this is one deficiency of the current standard of care addressed by the instant disclosure. Drilling into jawbone usually occurs in several separate steps. The pilot hole is expanded by using progressively wider drills (typically between three and seven successive drilling steps, depending on implant width and length). Care is taken not to damage the osteoblast or bone cells by overheating. A cooling saline or water spray keeps the temperature of the bone to below 47° C. (approximately 117 degrees Fahrenheit). The implant screw is screwed into place at a precise torque so as not to overload the surrounding bone (overloaded bone can die, a condition called osteonecrosis, which may lead to failure of the implant to fully integrate or bond with the jawbone). Despite the state of the art in dental implants, there are numerous circumstances that can result in failure. One particular source of failure is insufficient bone tissue at the site, which complicates the process of drilling into the jaw, as well as the ability of the dental implant to osseointegrate. One feature of the present disclosure is that the disclosed compositions are useful for promoting bone reconstruction at a site, such as a dental bone cavity. By promoting bone reconstruction prior to placement of a dental implant, the methods and compositions of the disclosure significantly improve the long term success of the implant. Additionally, these methods and compositions help decrease the amount of time required for implant anchorage following placement, thereby allowing subsequent placement of restorative devices (e.g., crowns, bridges) with less delay following placement of the implant. Finally, the compositions and methods of the disclosure expand the patient populations suitable for having a dental implant and make the procedure a tangible treatment option for patients who otherwise have insufficient bone for proper placement of the device.

Additionally, before describing the method in additional detail, it should be noted that compositions of the disclosure may also be used in other contexts outside preparation for a dental implant. For example, bone reconstruction in the jaw may be necessary to help preserve or even rebuild facial structures and features following injury or disease. The compositions of the disclosure may be similarly used in those contexts.

In certain aspects and embodiments, the disclosure provides a method of applying a composition to a dental bone cavity or to a portion of jaw bone. A layer of a composition of the disclosure is applied to the site where bone reconstruction is desired, e.g. in the dental bone cavity. The thickness of the layer may vary depending on the site and type of reconstruction. For example, a layer may be about 0.5-4 millimeters. Following application of a layer, the applied composition is irradiated with actinic light. Exemplary light useful for this purpose is visible light having a wavelength of 400-800 nm. The steps of applying a layer of composition and then irradiating with actinic light may be repeated at least 2, 3, 4 or at least 5 times, depending on the particular application and needs of the patient. The layered composition may be putty-like and is not washed away by fluid in the mouth. Alternatively, the layered composition may be covered or sutured loosely to help keep it in place. When more than one layer is applied, each layer may comprise a different ratio of hydroxyapatite to hyaluronic acid, and accordingly each layer may have a different consistency. For example, the first layer may have a first consistency, the second layer may have a second consistency and the third layer may have a third consistency. For example, the first layer may be flowable and the second layer may be putty-like and the third layer may be rigid. Over a period of time, such period depending on the amount of composition introduced at the site, the layered composition of the disclosure biodegrades and is replaced by bone. Prior to applying the composition to the bone cavity, the bone cavity may be treated for possible infection using any suitable treatment such as applying a composition having antimicrobial properties. Debridement of the bone cavity walls may also be performed before application of the composition.

Over time, bone tissue replaces the composition. As this is occurring, the composition itself is biodegrading. As a result, bone reconstruction occurs at the site. When sufficient bone reconstruction has occurred, a dental implant may optionally be installed in the jaw—at this site where the amount of bone tissue has been augmented.

The compositions of the present disclosure may also be used in non-dental clinical applications, such as spinal procedures and orthopedic procedures.

The composition is typically administered to a patient in a clinical setting. In certain embodiments, the composition is administered during a surgical procedure. The composition may be placed at a treatment site, such as an implant site, by molding, placing, injecting, or extruding the composition into the treatment site.

Any bone disease or disorder may be treated using the composition of the present disclosure including genetic diseases, congenital abnormalities, fractures, iatrogenic defects, bone cancer, bone metastases, inflammatory diseases (e.g. rheumatoid arthritis), autoimmune diseases, metabolic diseases, and degenerative bone disease (e.g., osteoarthritis). In certain embodiments, the compositions are formulated for the repair of a simple fracture, compound fracture, or non-union; as an external fixation device or internal fixation device; for joint reconstruction, arthrodesis, arthroplasty, or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; for revision surgery; for revision surgery of a total joint arthroplasty; and for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

The composition may be made flowable before it is administered to a subject. This allows the composition to fit into irregularly shaped sites. In certain embodiments, the composition is injected or extruded into a tissue site (e.g., a bony defect or bone cavity). For example, the composition may be injected using a needle and syringe. The syringe may be driven by hand or mechanically. In some embodiments, the mixture is injected percutaneously. A bony injection site may be some distance from the skin, necessitating a longer needle. In other embodiments, the injection site may be exposed, for example, during surgery. In these cases a very short cannula may suffice for delivery of the mixture, and a wider bore cannula may be appropriate.

As detailed throughout the specification, compositions of the disclosure comprise a photoactivator (e.g. a fluorescent dye such as eosin Y); a calcium phosphate mineral; hyaluronic acid (such as cross-linked or non-crosslinked hyaluronic acid) and optionally glucosamine. Any of the compositions of the disclosure may be used in any of the methods described herein.

For example, in the case of knee replacement operations, a femoral and a tibial component are inserted into the distal end of the femur and the surgically prepared end of the tibia, respectively. The composition of the present disclosure may be layered, packed, or injected between the femoral and/or tibial components of the prosthesis and the respective portions of the femur and tibia. In this manner, as bone formation is induced between the prosthesis and the bones, the prosthesis becomes anchored.

In a further examples, the composition of the present disclosure is used to treat bone fractures traumatic osseous defects, or surgically-created osseous defects. When used for such treatment, the composition may be block-like, putty-like or flowable and is layered, packed, or injected into the fracture or defect. In this manner, as bone formation is induced, the fracture or defect is treated.

In a further example, the composition of the present disclosure is used to treat osteoporosis. When used for such treatment, the composition is typically in a more flowable form and is injected in existing bone to offset the effects of osteoporosis in which bone density is lost.

As noted above, the composition may be applied in a series of layers. For most applications, each layer is typically applied at a thickness of about 0.5-4 millimeters. In certain embodiments, each layer of composition is applied at a thickness of about 0.5, 1, 1.5, 2, 2.5, 3, 3.5, or 4 millimeters. When multiple layers of compositions are applied, each layer may be the same or a differing thickness.

When a layer is irradiated with actinic light, it is irradiated for a period of 1 second to 5 minutes. The time of irradiation will depend on the emitted power density of the light source. Alternatively, the layer is irradiated until the composition is substantially photobleached. To determine photobleaching, the surgeon may use an appropriate filter that allows visualization of the fluorescence being emitted from the layer upon exposure to actinic light. The surgeon may position an appropriate filter over the treatment site to visualize fluorescence of the layer in real time. Photobleaching can be considered to be substantially complete when no further fluorescence can be observed.

When multiple layers of composition are applied, each layer may be irradiated for the same period of time or for differing periods of time. In other words, in certain embodiments, the time of irradiation is independently selected for each layer. Note that one exemplary source of actinic light is a dental lamp. By way of example, the actinic light used to irradiate each layer has a wavelength in the range of 400-800 nm (e.g., 400-500, 450-550, 425-525, 500-600, 550-650, 600-700, 650-750, or 700-800 nm). When multiple layers of composition are applied and irradiated, each layer may be irradiated with light having the same or differing wavelength. In other words, in certain embodiments, the wavelength of the light is independently selected for each layer that is irradiated. It should be noted that cross-linking of non-cross-linked hyaluronic acid, according to certain embodiments the disclosure, is not thought possible using visible light.

Any source of actinic light can be used. Any type of halogen, LED or plasma arc lamp, or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In yet another embodiment, a LED photocuring device is the source of the actinic light. In yet another embodiment, the source of the actinic light is a source of visible light having a wavelength between 400 and 700 nm. The light can be violet, blue, green, yellow, orange or red light, or a combination of these colours. Furthermore, the source of actinic light should have a suitable power density. Suitable power densities are in the range from about of about 0.1-500 mW/cm$^2$, about 0.1-200 mW/cm$^2$, about 1-200 mW/cm$^2$, about 1-150 mW/cm$^2$, about 1-100 mW/cm$^2$, about 30-150 mW/cm$^2$.

In addition to the foregoing dental and other clinical uses, compositions of the disclosure may be used for research purposes. In the research context, the compositions can be used when testing and developing improved dental implants and/or techniques for reconstructive intervention. Moreover, given that the compositions of the disclosure effectively promote growth, recruitment and/or maintenance of bone tissue, such compositions are useful in the study of bone and tissue growth, recruitment and/or maintenance.

EXAMPLES

The examples below are given so as to illustrate the practice of this invention. They are not intended to limit or define the entire scope of this invention.

Example 1

Preparation of Dental Paste 1.88 g of crossed-linked hyaluronic acid (Regenyal Idea) (about 36% of the total composition), 11.6 mg of Eosin Y (about 0.22% of the total composition) and 3.3 g of hydroxyapatite particles (about 64% of the total composition) were placed in a beaker and mixed with a spatula. 0.8-0.9 g of the mixture was placed into small glass vials (oblong shape). The vials were closed tightly with a rubber cap. A 10 ml syringe with a needle was used to remove the air from the vials. The vials were then sealed with a hard plastic cap and autoclaved at 120° C., 15 psi for 15 minutes. The resulting composition had the consistency of flexible clay and, following autoclaving, was sterile. This composition is an example of a composition having a putty-like consistency.

Example 2

Application of Dental Paste to Dental Bone Cavity

The dental paste prepared in Example 1 was applied to the dental bone cavity of 4 patients in a series of 2-3 layers having a thickness of 2 to 4 mm. Between applications, each layer was irradiated with actinic blue light for between 30 seconds and five minutes, preferably about 30-60 seconds. The dental paste emitted fluorescence light (which was visible to the eye when viewed through an orange filter) during light irradiation. This was repeated until the dental bone cavity was filed with the dental paste. Gums were sutured loosely to retain the dental paste in the cavity.

Example 3

Processing of Samples from the Filled Dental Bone Cavity

Samples of about 2-4 mm were taken from the site of the filled dental bone cavity of each patient after 3.5 months (patient 1), 4.5 months (patient 2), 5 months (patient 3) and 6 months (patient 4) post-implantation. Collected samples were fixed in formalin or ethanol, and subsequently decalcified using decalcifying solution (Solution Lite #D0818 from Sigma) for 16 hours. Following complete decalcification, the samples were embedded in paraffin and cut in 4 μm slices using a microtome (Leica, model RM 2255).

Example 4

Histological and Immunohistological Staining

The processed samples were stained using haemotoxylin and eosin (H+E), Goldner trichrome, OSF-2 and TRAP. Goldner trichrome is a histological stain that allows for sharp discrimination of mature bone matrix which stains green, immature new bone matrix which stains red, and calcified cartilage which stains very pale green. OSF-2 is a protein produced by muscle cells, fibroblasts and osteoblasts. In bone, OSF-2 is thought to be involved in osteoblast recruitment, attachment and spreading. An anti-human OSF-2 antibody can be used to detect the presence of OSF-2 in prepared bone transplant samples. The presence of OSF-2 indicates the presence of osteoblasts. TRAP is a protein produced by macrophages, osteoclasts, spleen and liver. An anti-human TRAP antibody can be used to detect the presence of TRAP in prepared bone transplant samples. The presence of TRAP indicates the presence of osteoclasts.

H+E staining showed the presence of osteocytes within lacunae, osteoclasts, bone lining cells (immature osteoblasts) and osteoblasts. As the samples were obtained by drilling some cytoplasm and nuclei appeared broken in some of the samples.

Figure 4A:
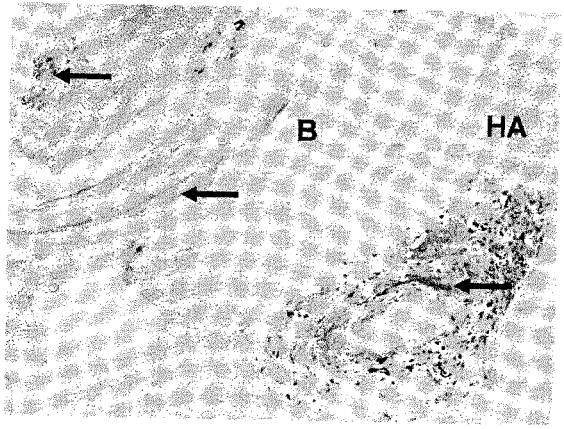
FIGS. 4A and 4B are immunostains (×500) of osteoblasts with OSF-2 marker in samples taken from bone cavity sites from Patients 2 and 4, respectively, implanted with a composition according to an embodiment of the present disclosure and described in Examples 1 to 5. 'B' indicates bone, and 'HA' indicates the composition according to an embodiment of the present disclosure.
Figure 4B:
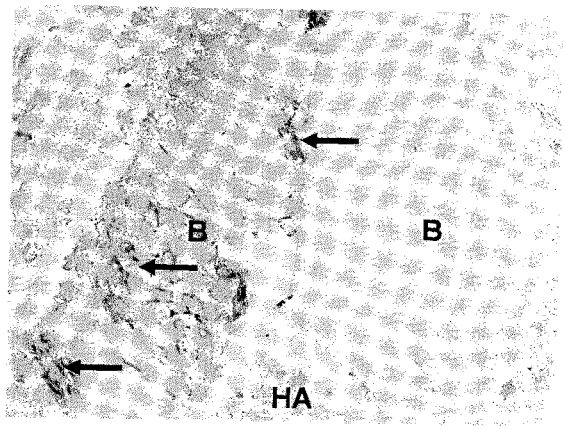

OSF-2-positive structures were detected in samples from all four patients indicating the presence of osteoblasts in the samples. FIG. 4 illustrates such OSF-2 positive structures in patients 2 and 4 (arrows point to bone cells). Similar histology was observed in patients 1 and 3 (not shown).

Figure 5A:
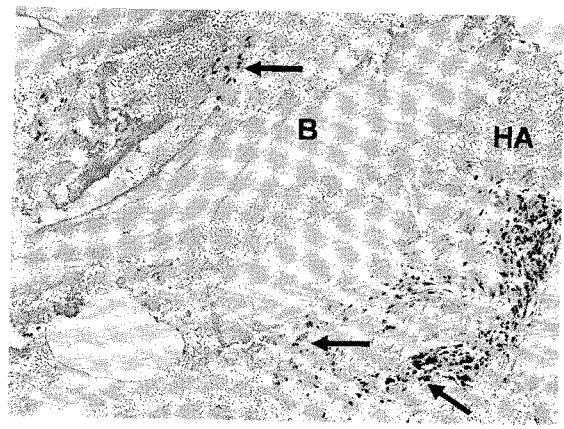
FIGS. 5A and 5B are immunostains (×500) of osteoclasts with TRAP marker in samples taken from a bone cavity sites from Patients 2 and 4, respectively, implanted with a composition according to an embodiment of the present disclosure and described in Examples 1 to 5. 'B' indicates bone, and 'HA' indicates the composition according to an embodiment of the present disclosure.
Figure 5B:
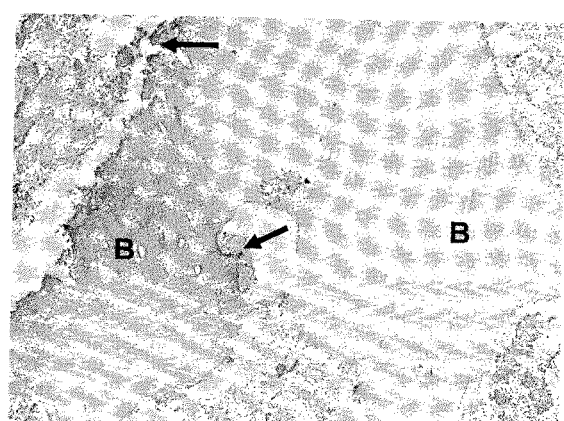

TRAP-positive structures were also detected in samples taken from all four patients, indicating the presence of osteoclasts in the samples. FIG. 5 illustrates such TRAP-positive structures in patients 2 and 4 (arrows point to bone cells). Similar histology was observed in patients 1 and 3 (not shown).

Figure 6A:
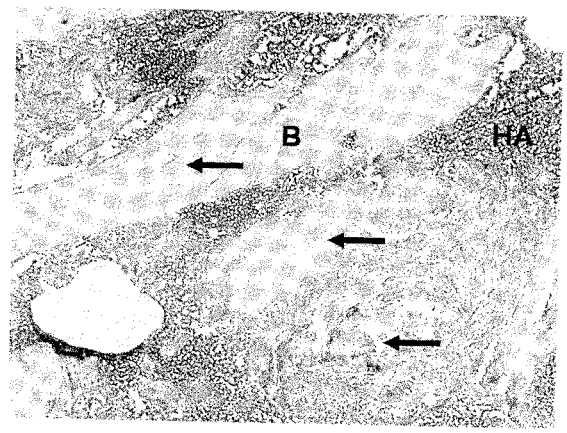
FIGS. 6A and 6B are goldner trichrome stains (×500) in samples taken from bone cavity sites from Patients 2 and 4, respectively, implanted with a composition according to an embodiment of the present disclosure and described in Examples 1 to 5. 'B' indicates bone, and 'HA' indicates the composition according to an embodiment of the present disclosure.
Figure 6B:
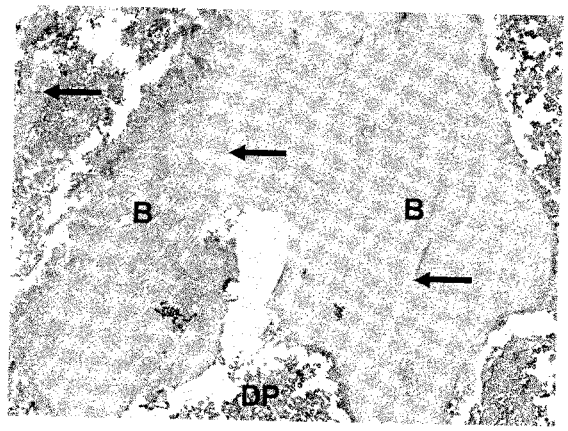

Goldner trichrome staining revealed that new bone formation was present in the bone cavity of all four patients which were filled with a composition according to an embodiment of the present invention, as evidenced by the presence of green staining. FIG. 6 illustrates examples of goldner trichrome stained samples from patients 2 and 4 (arrows point to bone cells). Similar histology was observed in patients 1 and 3 (not shown). The level of mineralization in lamellar structures is observed by different layers showing shades from lilacs to green. Other non-bone structures can be attributed to residual dental paste (burgundy color). Lacunaes are clearly seen in the bone structures.

These results indicate that the dental paste of the present disclosure allows for bone formation in the bone cavity at least 3.5 months following placement in the bone cavity, and possibly earlier. Osteoblasts and osteoclasts are present at the implant site as evidenced by the presence of OST-2 and TRAP immunostaining in explant samples. Goldner Trichrome staining demonstrated the presence of bone with lamellar structures. In all four patients, the bone defect site maintained its structure and did not collapse.

Example 5

Image Analysis and Percentage of New Bone Formation

Micrographs of the samples of Example 4 were taken and the images analysed (at a magnification of ×250) using Image-Pro Plus 4.1 (Media Cybernetics, Maryland, USA) in order to calculate the percentage of new bone formation. The results are presented in Table 1.

TABLE 1

Summary of percentage of new bone formed in the bone defect of 4 patients filled with a dental paste according to an embodiment of the present disclosure.

| Patient No. | Time of implantation/months | % new bone (mean) |
|---|---|---|
| 1 | 3.5 | 40 (n = 6) |
| 2 | 4.5 | 41 (n = 4) |
| 3 | 5 | 51 (n = 5) |
| 4 | 6 | 52 (n = 5) | n is the number of different portions from the same sample from each patient which were analysed.

Example 6

Preparation of Dental Paste

Dental paste was prepared having a composition similar to that of Example 1, except non cross-linked hyaluronic acid having a particle size of less than 500 nm was used as well as glucosamine. The dental paste was sterilized according to Example 1. The dental paste was applied to the dental bone cavity of two patients (patients 5 and 6) in the same manner as described in Example 2 above. Samples from the filled bone cavity site of patient 5 were removed after 7 months by drilling as before. For patient 6, a sample from the filled bone cavity site was removed after 3 months using a trephine burr having a cylindrical bore to obtain an intact cylindrical sample. The samples were processed as in Examples 4 and 5 above for histological staining and new bone formation analysis.

As for patients 1-4 above, osteoblasts, osteoclasts and new bone formation were observed in the filled bone cavity site of patients 5 and 6. The results are presented in Table 2 below.

TABLE 2

Summary of percentage of new bone formed in the bone defect of patients filled with dental paste according to an embodiment of the present disclosure.

| Patient No. | Time of implantation/months | % new bone (mean) |
|---|---|---|
| 5 | 7 | 47 (n = 7) |
| 6 | 3 | 34 (n = 10) | n is the number of different portions of the same sample from the same patient which were analysed.

Figure 7A:
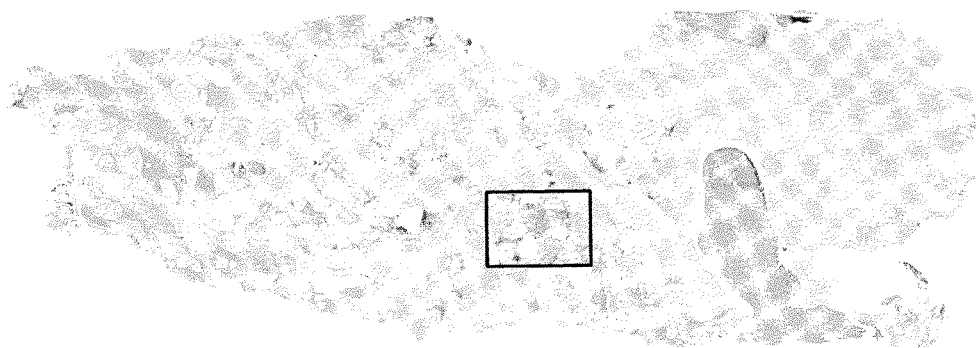
FIG. 7A is a goldner trichrome stain (×100) of a sample taken from a bone cavity site from Patient 6 implanted with a composition according to an embodiment of the present disclosure and described in Example 6.
Figure 7B:
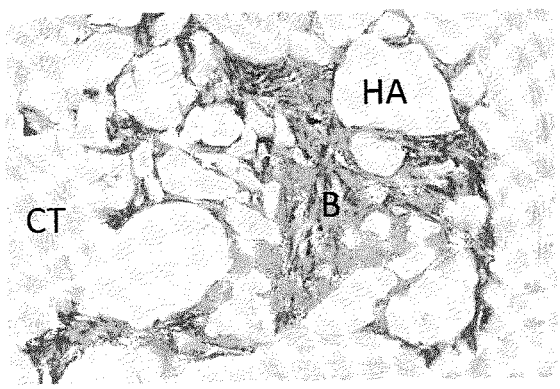
FIG. 7B is a higher magnification view (×500) of a central region of the sample of FIG. 7A (marked by the square) and stained by goldner trichrome. 'B' indicates bone, 'CT' indicates connective tissue, and 'HA' indicates the composition according to an embodiment of the present disclosure.
Figure 7C:
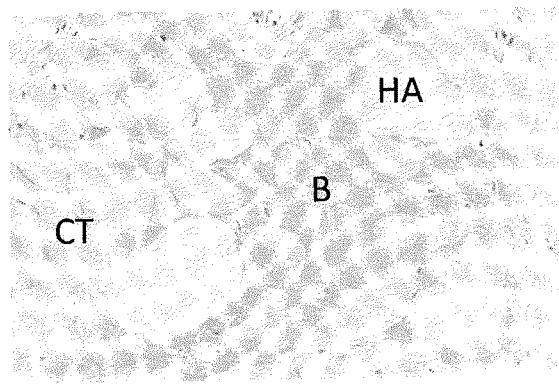
FIG. 7C is a higher magnification view (×500) of a central region of the sample of FIG. 7A (marked by the square) and stained by haemotoxylin and eosin. 'B' indicates bone, 'CT' indicates connective tissue, and 'HA' indicates the composition according to an embodiment of the present disclosure.

For patient 6, the obtained explanted material had a cross-sectional surface area of about $6 \times 10^6$ $\mu m^2$ (FIG. 7A). The left hand side of FIG. 7A was the bone (jaw) end of the cylindrical sample, and the right hand side of FIG. 7B was the gum end of the sample. At the bone end of the sample, there was observed a higher new bone content and more fragmentation of the dental paste material than at the gum end.

Although the examples above use Eosin Y as the photoactivator, it is thought that any other photoactivator which can absorb and emit light (e.g. can fluoresce) can also be used as the photoactivator of the present composition due to the beneficial effects of the emitted light. Any suitable photoactivating light having a wavelength which can activate the photoactivator can be used.

INCORPORATION BY REFERENCE

All publications and patents mentioned herein are hereby incorporated by reference in their entirety as if each individual publication or patent was specifically and individually indicated to be incorporated by reference. Citation or discussion of a reference herein shall not be construed as an admission that such is prior art to the present invention.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A biophotonic composition comprising:
   a photoactivator which can absorb and emit light;
   a calcium phosphate mineral having an average particle size of between about 150 nm and about 500 nm;
   hyaluronic acid; and
   glucosamine;
   wherein the hyaluronic acid and the glucosamine components are about 70-90% by weight of the total weight of the composition;
   wherein the biophotonic composition is non-photo-polymerized and is suitable for administration at a site of bone reconstruction;
   wherein the biophotonic composition emits fluorescence upon being illuminated by actinic light for a period of between about 1 second and 30 seconds; and
   wherein the biophotonic composition does not include an oxidant.

2. The biophotonic composition of claim 1, wherein the photoactivator is present in an amount of at least about 0.2% by weight of the total weight of the biophotonic composition.

3. The biophotonic composition claim 1, wherein the photoactivator is present in an amount of about 0.2-1% by weight of the total weight of the biophotonic composition.

4. The biophotonic composition of claim 1, wherein the photoactivator is a xanthene dye or a fluorescein derivative.

5. The biophotonic composition of claim 4, wherein the fluorescein derivative is eosin Y.

6. The biophotonic composition of claim 1, wherein the calcium phosphate mineral comprises hydroxyapatite.

7. The biophotonic composition of claim 1, wherein the calcium phosphate mineral is about 10-30% by weight of the total weight of the biophotonic composition.

8. The biophotonic composition of claim 1, wherein the hyaluronic acid is cross-linked hyaluronic acid.

9. The biophotonic composition of claim 1, wherein the hyaluronic acid is a non cross-linked hyaluronic acid.

10. The biophotonic composition of claim 9, wherein the hyaluronic acid has a molecular weight of between about 1 million Dalton and 2 million Dalton, about 1.2 million to about 1.8 million Dalton, or about 1.7 million Dalton.

11. The biophotonic composition of claim 1, wherein the hyaluronic acid is about 5-90% by weight of the total weight of the biophotonic composition.

12. The biophotonic composition of claim 1, wherein the ratio of calcium phosphate mineral to hyaluronic acid is about 1:9, 1.5:8.5, 2:8, 2.5:7.5 or 3:7.

13. The biophotonic composition of claim 1, wherein the ratio of calcium phosphate mineral to hyaluronic acid is about 6:4, 6.5:3.5 or 7:3.

14. The biophotonic composition of claim 1, wherein the ratio of calcium phosphate mineral to hyaluronic acid is about 8:2, 8.5:1.5, 9:1 or 9.5:0.5.

15. The biophotonic composition of claim 1, wherein the ratio of hyaluronic acid to glucosamine is about 1:1, 3:2, 7:3, 4:1; or 9:1.

16. The biophotonic composition of claim 1, wherein the ratio of calcium phosphate mineral to hyaluronic acid and glucosamine is about 1:9, 1.5:8.5, 2:8, 2.5:7.5 or 3:7.

17. The biophotonic composition of claim 1, wherein the ratio of calcium phosphate mineral to hyaluronic acid and glucosamine is about 6:4, 6.5:3.5 or 7:3.

18. The biophotonic composition of claim 1, wherein the ratio of calcium phosphate mineral to hyaluronic acid and glucosamine is about 8:2, 8.5:1.5, 9:1 or 9.5:0.5.

19. The biophotonic composition of claim 1, wherein the biophotonic composition does not include one or more of triethanolamine (TEA), N-vinyl-2-pyrrolidone (NVP), or N-vinyl caprolactam (NVC).

20. The biophotonic composition of claim 1, wherein the biophotonic composition does not include a 15 amino acid residue peptide irreversibly bound to the calcium phosphate mineral.

21. The biophotonic composition of claim 20, wherein the calcium phosphate mineral comprises hydroxyapatite.

22. A method for augmenting, repairing or regenerating bone, comprising:
   a) providing a biophotonic composition of claim 1;
   b) applying a layer of the biophotonic composition to a bone tissue site;
   c) irradiating the biophotonic composition with actinic light; and d) repeating steps (b) and (c) at least once.

23. The method of claim 22, wherein each layer of step (b) has a thickness of about 0.5-4 mm.

24. The method of claim 22, wherein the biophotonic composition is irradiated for less than about 5 minutes.

25. The method of claim 22, wherein the biophotonic composition is irradiated with light having a wavelength in the range of about 400-700 nm.

26. The method of claim 22, wherein the biophotonic composition promotes detectable bone growth in the bone tissue site in about 3 months.

27. The method of claim 22, wherein the biophotonic composition used for a first layer has a different ratio of calcium phosphate mineral to hyaluronic acid and/or glucosamine than the biophotonic composition used for a second layer.

* * * * *